United States Patent [19]

Gray

[11] Patent Number: 5,086,916

[45] Date of Patent: Feb. 11, 1992

[54] COMBINATION TOOTHBRUSH STERILIZATION CONTAINER AND MOUNTING BRACKET

[76] Inventor: Ruben L. Gray, 5853 Cedar Ave., Philadelphia, Pa. 19143

[21] Appl. No.: 633,656

[22] Filed: Dec. 21, 1990

[51] Int. Cl.$^5$ .................... B65D 81/24; A45D 44/18
[52] U.S. Cl. .................. 206/209.1; 206/209; 206/362; 206/362.1; 132/308; 132/310; 248/111; 248/225.2
[58] Field of Search .............. 206/362, 362.1, 362.3, 206/209.1, 209, 581; 312/207; 248/110, 111, 108, 225.2; 132/308, 310

[56] References Cited

U.S. PATENT DOCUMENTS

| | | | |
|---|---|---|---|
| D. 234,036 | 1/1975 | Nixon | D6/94 |
| 1,283,403 | 10/1918 | Eustis . | |
| 1,676,756 | 7/1928 | Weichsel . | |
| 1,743,646 | 1/1930 | Alderman, Jr. . | |
| 1,981,383 | 11/1934 | Feldon | 99/18 |
| 1,987,472 | 1/1935 | Feldon | 206/15.1 |
| 2,012,685 | 8/1935 | Posea | 206/15.1 |
| 2,148,043 | 2/1939 | Zero | 312/112.5 |
| 2,443,769 | 6/1948 | Huber | 21/83 |
| 2,720,439 | 10/1955 | Cristoval | 206/362.1 X |
| 2,794,696 | 6/1957 | Alves | 206/362.1 X |
| 3,685,660 | 8/1972 | Saunders | 211/60 R |
| 3,717,258 | 2/1973 | McKinnon | 248/225.2 X |
| 3,881,868 | 5/1975 | Duke | 21/83 |
| 4,396,238 | 8/1983 | Torruella | 248/111 X |
| 4,473,152 | 9/1984 | Jump, Jr. et al. | 206/209.1 |
| 4,816,205 | 3/1989 | Gallix | 248/225.2 X |
| 4,995,509 | 2/1991 | Kornfeind | 206/362 X |

*Primary Examiner*—Paul T. Sewell
*Assistant Examiner*—Ted Kavanaugh
*Attorney, Agent, or Firm*—Panitch, Schwarze, Jacobs & Nadel

[57] ABSTRACT

A toothbrush sterilization container and mounting bracket for sterilizing toothbrushes. The container includes a sterilization agent compartment, a toothbrush holder compartment, and a reservoir for the sterilization agent. The sterilization agent compartment has a first access opening permitting access to the sterilization agent compartment. The toothbrush holder compartment includes dividers for dividing the toothbrush holder compartment into individual toothbrush receiver compartments. The toothbrush holder compartment has a lid to provide access to the interior portions of the individual toothbrush receiver compartments. A shelf is provided below the container for receiving a tube of toothpaste. A mounting bracket is provided for mounting the container to a wall.

7 Claims, 2 Drawing Sheets

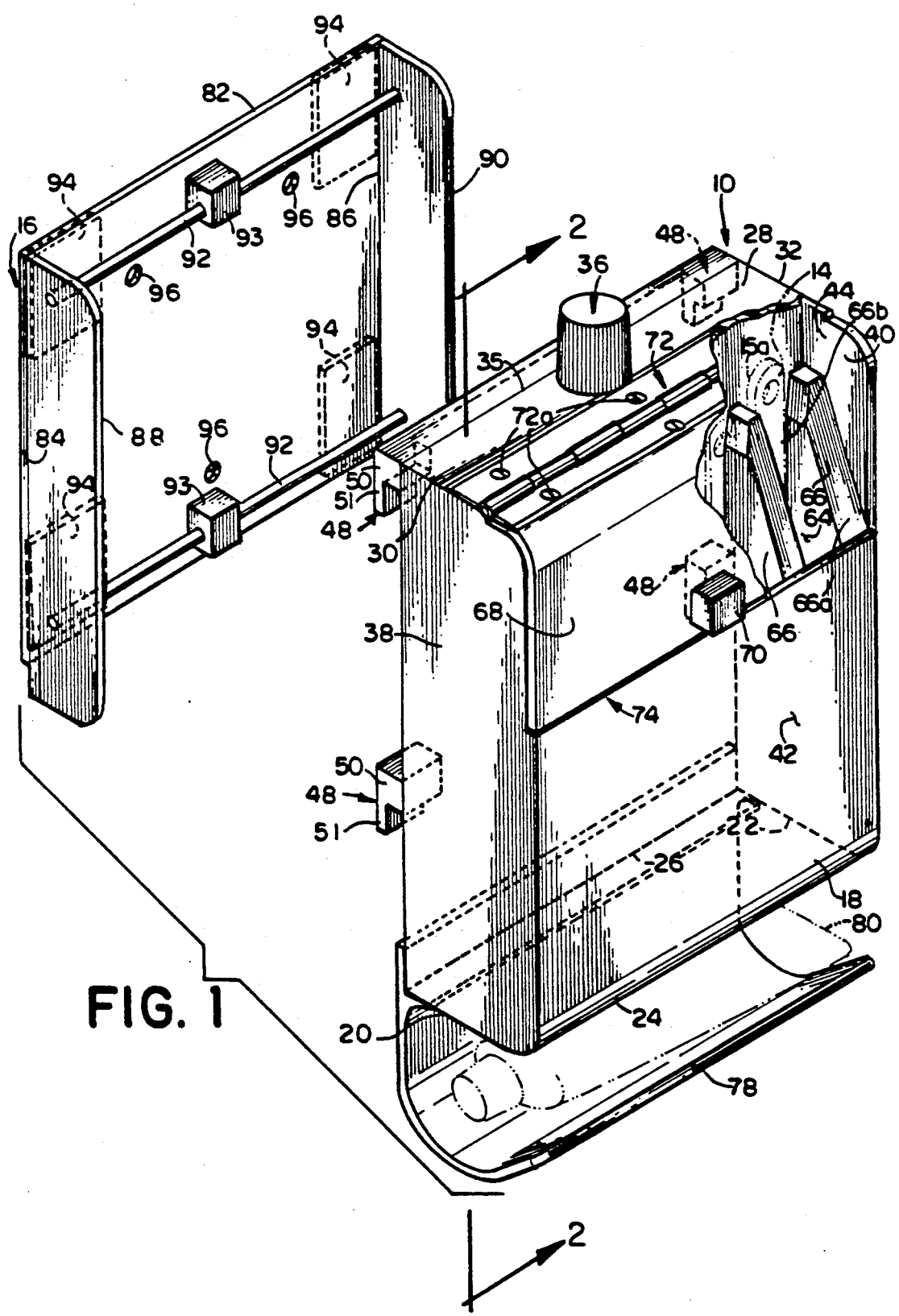

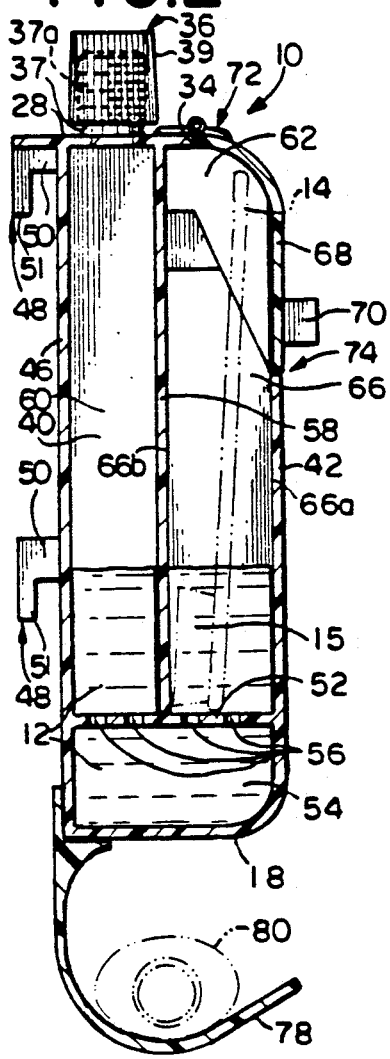
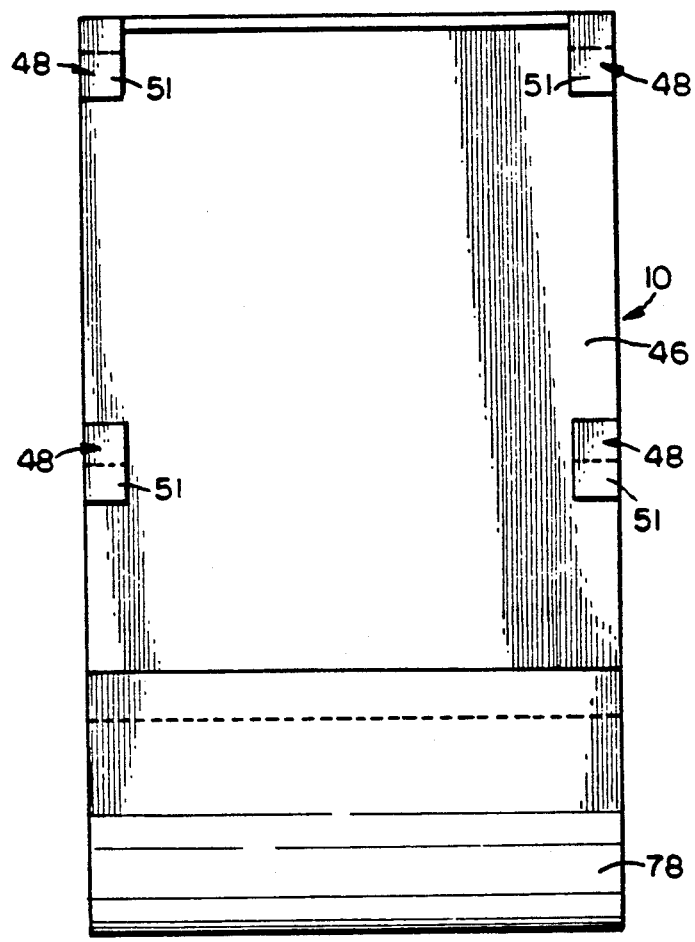
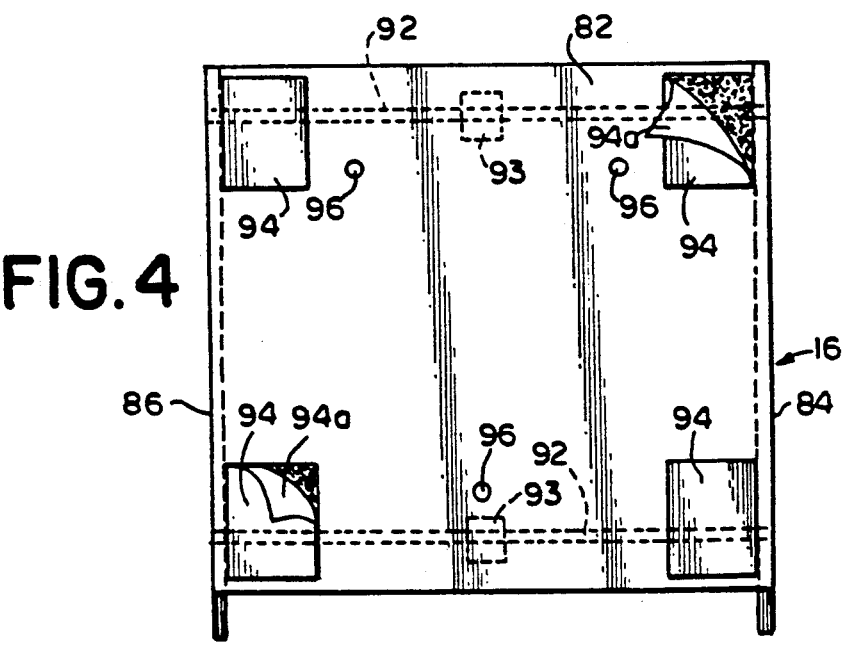

COMBINATION TOOTHBRUSH STERILIZATION CONTAINER AND MOUNTING BRACKET

FIELD OF THE INVENTION

The present invention relates to toothbrush sterilization containers, and more particularly to a toothbrush sterilization container and mounting bracket therefor.

BACKGROUND OF THE INVENTION

Typical toothbrush sterilization containers allow sterilization of toothbrushes by contacting the bristle portion of the toothbrush with a sterilization agent or with the fumes emanating from a volatile sterilization agent, such as an antiseptic.

Toothbrush sterilization containers are generally known in the art. One type of toothbrush sterilization container includes a brush holder connected by a recess to a well. The well is designed to accommodate a bottle containing a liquid sterilization agent. The sterilizing liquid flows from the bottle through the recess to the toothbrush sterilization chamber, where the liquid is maintained at a constant level. The supply of sterilizing liquid in the brush holder is thereby automatically replenished from the supply in the bottle as it is used.

Another type of toothbrush sterilization container provides separate compartments for receiving toothbrushes and a sterilization liquid. The compartments are separated by a partition forming a false bottom. Fumes from the sterilizing or desiccating agent are allowed to contact the toothbrushes by means of openings in the false bottom. A hinge lid covers the receptacle as a dust barrier.

Another antiseptic toothbrush container which is disclosed in the prior art, has a partition dividing it into two compartments. The rear compartment receives a sterilization agent and the front compartment receives toothbrushes. The wall between the rear compartment and the front compartment has ports which allow sterilizing fumes to pass to the brushes.

Yet another type of toothbrush sterilization container includes a sterilization chamber containing a sterilization agent, into which a toothbrush may be dipped, and a ventilating chamber in which the bristle portion of the brush may dry. The toothbrush sterilization container is provided with a holder which may be supported on a wall.

A toothbrush holder with a mounting means is also disclosed in the prior art. The mounting means consists of a rectangular plate secured to a wall by conventional methods such as by glue or adhesives. Cutouts in the plate form tongues which provide means for receiving and supporting the housing of the toothbrush holder by a beam and a web which rest on the tongues.

The present invention overcomes the disadvantages inherent in the prior art by providing a toothbrush sterilization container that is both durable and easy to manufacture. The container lid has been designed to inhibit evaporation or contamination of the sterilizing agent while providing ready access to toothbrushes and facilitating cleaning of the container. The container includes individual compartments to aid in preventing direct contact between individual toothbrushes. The divider panels which separate each individual compartment are angled and tapered at the top to facilitate removal of toothbrushes. The divider panels are designed such that a person can slip a finger or other object behind the end of a toothbrush in an individual compartment to tip the toothbrush forward and, thereby aid in removal of the toothbrush from the compartment. The container has a shelf for holding a tube of toothpaste in convenient proximity to the toothbrushes.

The mounting bracket allows the container to be mounted to a generally flat surface, such as a wall. A sterilization agent can be conveniently added to the interior portion of the container through a closable access opening while the container is mounted on the mounting bracket. The container may be easily removed from the bracket by sliding the container upward, away from the bracket. The mounting bracket itself may be attached to the wall by such means as adhesives or fasteners. Adhesives may be used, for example, in situations where it is desirable to not penetrate the surface of the wall. Fasteners may be used for more permanent mounting of the bracket to the wall, or as additional means for securing the mounting bracket to the wall.

SUMMARY OF THE INVENTION

Briefly stated, the present invention comprises a toothbrush sterilization container and mounting bracket. The mounting bracket may be used for attaching the toothbrush sterilization container to a generally flat surface. The toothbrush sterilization container receives a sterilization agent and at least one toothbrush. The container includes a bottom wall having a first edge, a second edge, a third edge, and a fourth edge. The container further includes a top wall having a first edge, a second edge, a third edge and a fourth edge. The top wall is positioned generally parallel and spaced from the bottom wall. The top wall has a first access opening for adding and removing the sterilization agent from the container. The container also includes a first side wall extending between and attached to the first edges of the top and bottom walls such that the first side wall extends generally perpendicularly from the top and bottom walls. The container also includes a second side wall extending between and attached to the second edges of the top and bottom walls such that the second side wall extends generally perpendicularly from the top and bottom walls. The container further includes a front wall extending from the third edge of the bottom wall such that a second access opening for adding and removing toothbrushes from the container is formed between the front and top walls. The front wall extends generally perpendicularly from the bottom wall. The container also includes a rear wall extending between and attached to the fourth edges of the top and bottom walls such that the rear wall extends generally perpendicularly from the top and bottom walls. The rear wall has bracket means for attaching the container to the mounting bracket. The container further includes a first partition positioned between and spaced from the top and bottom walls and in complementary engagement with the front wall, the rear wall, the first side wall and the second side wall such that the a reservoir is formed between the bottom wall, the first partition, the first side wall, the front wall, the second side wall, and the rear wall. The first partition includes openings therethrough for permitting the sterilization agent to pass to and from the reservoir. The container also includes a second partition positioned between and spaced from the front and rear walls and in complementary engagement with the first partition, the top wall, the first side wall and the second side wall such that a sterilization agent compartment is formed between the second partition, the rear wall, the first partition, the top wall, the first side wall and the second side wall and a toothbrush holder compartment is formed between the second partition, the first partition, the front wall, the first side wall, and the second side wall. Divider means is positioned within the toothbrush holder compartment for dividing the toothbrush holder compartment into individual toothbrush receiver compartments and interior portions thereof. The container further includes a lid member for being pivotally mounted to the top wall and hinge means interconnected between the lid member and the top wall for allowing the lid member to pivot with respect to the top wall between a first position wherein the lid member is positioned proximate the second access opening and a second position wherein the lid member is positioned away from the second access opening. A shelf member extends from the bottom wall of the toothbrush sterilization container for receiving a toothpaste tube, whereby a sterilization deposited within the sterilization agent compartment through the first access opening flows through a portion of the openings in the first partition into the reservoir and upon the reservoir being filled with the sterilization agent, the sterilization agent flows through another portion of the openings in the first partition into the toothbrush holder compartment to thereby sterilize any toothbrushes therein. The container may be combined with a mounting bracket for attaching the container to a generally flat surface. The mounting bracket comprises a support plate having a first side edge and a second side edge. The mounting bracket further includes a first side plate extending from the first side edge of the support plate such that the first side plate and the support plate are generally perpendicular with respect to each other. The mounting bracket also includes a second side plate extending from the second side edge of the support plate such that the first side plate and the support plate are generally perpendicular with respect to each other and the first side plate and the second side plate are generally parallel with respect to each other. The mounting bracket includes a bar extending between the first side plate and the second side plate. The bar is spaced from the support plate a predetermined distance to thereby define a space therebetween for complementarily receiving the bracket means within the space when the container is positioned on the mounting bracket. The mounting bracket further comprises mounting means positioned on the support plate for attaching the support plate to the generally flat surface.

BRIEF DESCRIPTION OF THE DRAWINGS

The foregoing summary, as well as the following detailed description of the preferred embodiment, will be better understood when read in conjunction with the appended drawings. For the purpose of illustrating the invention, there is shown in the drawings an embodiment which is presently preferred, it being understood, however, that the invention is not limited to the specific methods and instrumentalities disclosed. In the drawings:

FIG. 1 is an exploded perspective view partially broken-away, of a toothbrush sterilization container and mounting bracket in accordance with the present invention;

FIG. 2 is a cross-sectional view of the toothbrush sterilization container of FIG. 1 taken along line 2—2 of FIG. 1;

FIG. 3 is a rear elevational view of the toothbrush sterilization container of FIG. 1; and FIG. 4 is a rear elevational view of the mounting bracket of FIG. 1.

DESCRIPTION OF THE PREFERRED EMBODIMENT

Certain terminology is used in the following description for convenience only and is not limiting. The words "right," "left," "top," "bottom," "front," and "rear" designate directions in the drawings to which reference is made. The terminology includes the words above specifically mentioned, derivatives thereof, and words of similar import.

Referring to the drawings, wherein like numerals indicate like elements throughout, there is shown in FIGS. 1 through 4 a preferred embodiment of a toothbrush sterilization container 10, for receiving a sterilization agent 12 and at least one toothbrush 14, and a mounting bracket 16.

The sterilization agent 12 is preferably comprised of an antiseptic or antibacterial agent, such as ethanol. However, one of ordinary skill in the art understands that the sterilization agent 12 may be comprised of any agent with sterilizing properties, such as an alcohol.

In the present embodiment, the toothbrush sterilization container 10 is preferably formed of a polymeric material, such as polyvinyl chloride, to enhance durability and reduce the cost of manufacture. However, it is understood by those skilled in the art that the present invention may be formed from any plastic, such as polypropylene, polyethylene, or a combination of plastics, metal, wood, or any other material impervious to penetration by the sterilization agent 12.

In the presently preferred embodiment, the container 10 and mounting bracket 16 are formed from the same material (e.g., polyvinyl chloride) unless otherwise indicated hereinafter. But one of ordinary skill in the art readily understands that parts of the container 10 or mounting bracket 16 may be formed from other materials.

It is preferred that the container 10 be shaped in a generally parallelepiped manner, as exemplified by the present embodiment. However, one of ordinary skill in the art understands that the general shape of the container 10 could be cylindrical, octagonal, trapezoidal, or any other shape in keeping with the spirit and scope of the present invention.

Referring now to FIGS. 1 and 2, the toothbrush sterilization container 10 is preferably comprised of a bottom wall 18 having a first edge 20, a second edge 22, a third edge 24, and a fourth edge 26. In the present embodiment, the edges 20, 22, 24, and 26 of the bottom wall 18 form a generally rectangular bottom wall 18 in plan view. However, one of ordinary skill in the art understands that the bottom wall 18 could be of other geometrical configurations in plan view, including trapezoidal and triangular.

In the present embodiment, it is preferred that the container 10 further includes a top wall 28 having a first edge 30, a second edge 32, a third edge 34, and a fourth edge 35. The top wall 28 is preferably positioned generally parallel to and spaced from the bottom wall 18. The top wall 28, like the bottom wall 18, is generally rectangular in plan view. However, it is understood by the ordinarily skilled artisan that the top wall 28 could be of other geometrical configurations, such as trapezoidal or triangular.

As shown in FIGS. 1 and 2, the top wall 28 has a first access opening 36 for adding and removing the sterilization agent 12 from the container 10, as described in more detail hereinafter. In the presently preferred embodiment, the first access opening 36 comprises a generally cylindrical filler neck 37 having external threads 37a and a centrally disposed bore (not shown) therethrough for adding and removing the sterilization agent 12. A cap 39 having complementary internal threads is releasably positioned thereon for preventing dust and other foreign matter from entering the container 10 and to inhibit evaporation of the sterilization agent 12.

As best shown in FIG. 1, the container 10 preferably comprises a first side wall 38 extending between and attached to the first edge 30 of the top wall 28 and the first edge 20 of the bottom wall 18 such that the first side wall 38 extends generally perpendicularly from the top wall 28 and the bottom wall 18. Similarly, it is preferred that the container 10 further comprises a second side wall 40 extending between and attached to the second edge 32 of the top wall 28 and the second edge 22 of the bottom wall 18 such that the second side wall 40 extends generally perpendicularly from the top wall 28 and the bottom wall 18.

In the present embodiment, it is preferred that first and second side walls 38, 40 be generally rectangular in elevational view, except that the corners thereof proximate the top and bottom walls 28, 18 are generally arcuate for aesthetic purposes. It is understood by those skilled in that art that the first and second side walls 38, 40 could be of other geometrical configurations, such as trapezoidal or triangular.

Referring to FIG. 1, the container 10 further includes a front wall 42 extending from the third edge 24 of the bottom wall 18 such that a second access opening 44 for adding and removing toothbrushes 14 from the container 10 is formed between the front wall 42 and the top wall 28. As shown in FIG. 2, the front wall 42 preferably extends generally perpendicularly from the bottom wall 18. However, it is understood by those skilled in the art that the front wall 42 could extend from the bottom wall 18 at any angle, such as 80°. In the present embodiment, it is preferred that the front wall 42 be curved in elevational view at its bottom, to correspond with the generally arcuate shape of the corners of the first and second side walls 38, 40.

In the present embodiment, the container 10 preferably further comprises a rear wall 46 (see FIG. 2) extending between and attached to the fourth edge 35 of the top wall 28 and the fourth edge 26 of the bottom wall 18 such that the rear wall 46 extends generally perpendicularly from the top wall 28 and the bottom wall 18. As with the front wall 42, it is understood by those skilled in the art that the rear wall 46 could extend between the top and bottom walls 28, 18 at any angle.

Referring now to FIGS. 2 and 3, the rear wall 46 preferably includes bracket means for attaching the container 10 to the mounting bracket 16. In the presently preferred embodiment, the bracket means comprises four generally L-shaped members 48 extending outwardly from the rear wall 46. One of ordinary skill in the art understands that the bracket means could comprise a single generally L-shaped member 48 or as many generally L-shaped members 48 as desired.

As best shown in FIG. 2, the L-shaped members 48 include a first leg 50 extending outwardly and generally perpendicularly from the rear wall 46 and a second leg 51 extending generally perpendicularly and downwardly from the distal end of the first leg 50 for releasable attachment to the mounting bracket 16, as described in more detail hereinafter. It is understood by those of ordinary skill in the art that the L-shaped members 48 could be formed in any shape which would facilitate attachment to the mounting bracket 16, such as a hook or clamp.

Referring now to FIG. 2, in the presently preferred embodiment the container 10 preferably includes a first partition 52 positioned between and spaced from the top wall 28 and the bottom wall 18 and in complementary engagement with the front wall 42, the rear wall 46, the first side wall 38 and the second side wall 40. As shown in FIG. 2, the first partition 52 preferably extends generally parallel to the bottom wall 18 to thereby form a generally parallelepiped reservoir 54 between the bottom wall 18, the first partition 52, the first side wall 38, the front wall 42, the second side wall 40, and the rear wall 46. The first partition 52 includes openings 56 therethrough for permitting the sterilization agent 12 to pass to and from the reservoir 54.

The container 10 also preferably includes a second partition 58 positioned between and spaced from the front wall 42 and the rear wall 46 and in complementary engagement with the first partition 52, the top wall 28, the first side wall 38 and the second side wall 40. As shown in FIG. 2, the second partition 58 preferably extends generally parallel to the front and rear walls 42, 46 to thereby form a generally parallelepiped sterilization agent compartment 60 between the second partition 58, the rear wall 46, the first partition 52, the top wall 28, the first side wall 38 and the second side wall 40. A generally parallelepiped toothbrush holder compartment 62 is also formed between the second partition 58, the first partition 52, the front wall 42, the first side wall 38 and the second side wall 40. One of ordinary skill in the art understands that the sterilization agent compartment and the toothbrush holder compartment may be of any general shape corresponding to the general shape of the container, such as trapezoidal or triangular.

As shown in FIGS. 1 and 2, in the present embodiment, it is preferred that the container 10 include divider means positioned within the toothbrush holder compartment 62 for dividing the toothbrush holder compartment 62 into individual toothbrush receiver compartments 64 and interior portions thereof.

In the present embodiment, the divider means preferably comprises a series of panels 66 spaced apart from each other within the toothbrush holder compartment 62 for defining the individual toothbrush receiver compartments 64 therebetween. Each panel 66 includes a front edge 66a. The front edge 66a is attached to the front wall 42 of the container 10. Each panel 66 further includes a rear edge 66b which is attached to the second partition 58 of the container 10. The height of the rear edge 66b is less than the height of the second partition 58 to enable a person to readily grasp the end 15a of a toothbrush 14 placed in the individual toothbrush receiver compartment 64, as best shown in FIG. 2.

In addition, the front edge 66a is angled, from the point at which it attaches to the front wall 42, towards the point where the top of the rear edge 66b attaches to the second partition 58. The top of the front edge 66a, proximate the point of attachment of the top of the rear edge 66b to the second partition 58, is tapered in order to facilitate access to the ends of the toothbrushes 14. The tapering and angling of the front edge 66a greatly facilitates removal and addition of toothbrushes 14 to their individual toothbrush receiver compartments 64. By not extending the rear edge 66b the entire length of the second partition 58 of the container 10, toothbrushes 14 may be easily removed from the individual toothbrush receiver compartments 64. For example, if a toothbrush 14 is leaning against the second partition 58, in accordance with the present invention, a person can readily slip a finger or other object between the end 15a of the toothbrush 14 and the second partition 58 in order to pull the toothbrush 14 forward and ease extraction of the toothbrush.

As shown in FIG. 2, each panel 66 includes a bottom edge 66c which is attached to the first partition 52. The bottom edge 66c extends generally perpendicular to the front and rear edges 66a and 66b. By attaching the panel edges 66a, 66b, and 66c to the front wall 42, the second partition 58, and the first partition 52, respectively, it is possible to inhibit contact between the bristles 15 of the toothbrushes 14 and thereby decrease the risk of transmitting germs and dirt. Presently, it is preferred that the panels 66 be attached by adhesives, although one of ordinary skill in the art understands that the panels 66 may be attached by other means, such as by fasteners or by welding.

Each individual toothbrush receiver compartment 62 preferably accommodates at least one toothbrush 14 for sterilization. It is understood by those skilled in the art that the toothbrush holder compartment 62 can include any number of panels 64, including zero, three and five, for allowing the toothbrush holder compartment 62 to receive any number of toothbrushes 14. Moreover, it is preferred that the toothbrush holder compartment 62 be of sufficient height and depth to receive standard size toothbrushes completely therein.

Referring now to FIGS. 1 and 2, the container 10 includes a lid member 68 for being pivotally mounted to the top wall 28. In the present embodiment, it is preferred that the container 10 further include a handle 70 positioned on the lid member 68 for facilitating the movement thereof. As shown in FIG. 2, in the present embodiment, it is preferred that the lid member 68 be generally J-shaped in cross-section to thereby conform to the shape of the first and second side walls 38, 40. However, it is understood by those skilled in the art that the lid member could be constructed of other geometrical configurations so long as access to the toothbrush receiver compartments through the second access opening 44 is not unduly restricted.

In the presently preferred embodiment, the lid member 68 is sized to substantially cover the second access opening 44 to thereby inhibit evaporation of the sterilization agent 12. As a result, the sterilization agent 12 need not be frequently replenished. Further, the lid member 68 inhibits the contamination of the sterilization agent 12, toothbrush holder compartment 62, and toothbrushes 14 by inhibiting foreign matter from contacting the same.

The container 10 includes hinge means interconnected between the lid member 68 and the top wall 28 for allowing the lid member 68 to pivot with respect to the top wall 28 between a first position 74 wherein the lid member 68 is positioned proximate the second access opening 44 (i.e., closed) and a second position (not shown) wherein the lid member 68 is positioned away from the second access opening 44 (i.e., open). In the present embodiment, it is preferred that the hinge means comprise a single standard hinge 72 extending along the width of the top wall 28 and the lid member 68. However, it is understood by the ordinarily skilled artisan that a series of hinges could be interconnected between the lid member 68 and top wall 28 for accomplishing the same function. It is further understood that hinge means other than a standard hinge 72 could be used, for example, a flexible polymeric hinge (not shown).

In the present embodiment, it is preferred that the hinge 72 be formed from a lightweight high strength metallic material, such as stainless steel. It is understood by those skilled in the art, however, that other materials may be used to construct the hinge 72, such as brass, aluminum, and polymer(s).

In the present embodiment, it is preferred that the hinge 72 be connected to the top wall 28 and lid member 68 by a plurality of screws 72a spaced along the length of the hinge 72. However, it is understood by those skilled in the art that the hinge 72 can be secured to the top wall 28 and lid member 68 through other means, such as rivets or an adhesive.

As shown in FIGS. 1 and 2, the container 10 includes a shelf member 78 extending from the bottom wall 18 for receiving a toothpaste tube 80 (shown in phantom). The shelf member 78 is preferably J-shaped in cross-section for securely receiving a tube of toothpaste 80. However, it is understood by those skilled in the art that the shelf member 78 could be constructed in other geometrical figurations, such as generally L-shaped in cross-section.

In the present embodiment, it is preferred that the shelf member 78 be adhesively secured to the rear wall 46. However, it is understood by those skilled in the art that the shelf member 78 can be secured to the container 10 in a number of fashions, for instance, the shelf member 78 could be integrally formed with the container 10 during a molding process. It is further understood by those skilled in the art, that the present invention is not limited to the use of the shelf member 78. That is, the shelf member 78 can be omitted from the container 10 without departing from the spirit and scope of the invention.

Referring now to FIGS. 1 and 4, in the present embodiment it is preferred that a mounting bracket 16 be provided for attaching the container 10 to a generally flat surface (not shown), such as a wall. The mounting bracket 16 includes a generally planar support plate 82 having a first side edge 84 and a second side edge 86. A first side plate 88 extends from the first side edge 84 of the support plate 82 such that the first side plate 88 and the support plate 82 are generally perpendicular with respect to each other. A second side plate 90 extends from the second side edge 86 of the support plate 82 such that the second side plate 90 and the support plate 82 are generally perpendicular with respect to each other and the first side plate 88 and the second side plate 90 are generally parallel with respect to each other. It is preferred that the first and second side plates 88, 90 be generally rectangular in elevational view, except that the corners thereof are generally arcuate for aesthetic purposes.

The support plate 82 and first and second side plates 88, 90 are preferably sized to complementarily receive the container 10 therebetween. More particularly, the first and second side plates 88, 90 preferably extend from the support plate 82 a distance which is greater than the distance that the L-shaped members 48 extend from the rear wall 46, as described in more detail hereinafter.

In the presently preferred embodiment, the mounting bracket 16 is formed from the same type of material as the container 10, although one of ordinary skill in the art understands that the mounting bracket 16 may be formed from any material, such as metal, wood, and polymer(s).

As shown in FIG. 1, the mounting bracket 16 preferably includes a pair of spaced-apart bars 92 extending between the first side plate 88 and the second side plate 90. The bars 92 are spaced from the support plate 82 a predetermined distance to thereby define a space therebetween for complementarily receiving the bracket means within the space when the container 10 is positioned on the mounting bracket 16. That is, the second leg 51 of each L-shaped member 48 is slidable disposed within the space between the bars 92 and the support plate 82 when the container 10 is attached to the mounting bracket 16.

As shown in FIG. 1, each bar 92 includes a support block 93 which is adhesively secured to the support plate 82. Additionally, the bars 92 are supported by the first and second side plates 88, 90. That is, the first and second side plates 88, 90 include complementarily sized apertures therein for receiving the bars 92. The apertures and support block 93 serve to securely support the bars 92 on the mounting bracket 16.

While it is preferred that the mounting bracket 16 include a pair of bars 92, it is understood by those skilled in the art that any number of bars may extend between the first and second side plates 88, 90, such as one or three, without departing from the spirit and scope of the invention.

In the present embodiment, it is preferred that the bars 92 be constructed of a high strength metallic material, such as stainless steel or aluminum, although one of ordinary skill in the art readily recognizes that the bars 92 could be comprised of wood, polymer(s), or any other material in keeping with the general spirit and scope of the present invention.

The mounting bracket 16 includes mounting means positioned on the support plate 82 for attaching the support plate 82 to the generally flat surface. In a present embodiment, the mounting means preferably comprises an adhesive, such as double-sided tape 94, disposed between the support plate 82 and the generally flat surface, as is understood by those skilled in the art.

In addition the mounting means could further include one or more fasteners (not shown) positioned through apertures 96 in the support plate 82. The fasteners (e.g., self-tapping screws) are preferably secured to the generally flat surface to supplement the adhesive. One of ordinary skill in the art understands, however, that the mounting means could be comprised of the adhesive alone, the fasteners alone, or other different means of attaching the support plate 82 to the generally flat surface, such as magnets.

To install the mounting bracket 16 on the generally flat surface, the installer first marks the area upon which the mounting bracket 16 is to be mounted. The peelable-back portion 94a of the double-sided tape 94 is then removed. The support plate 82 is then placed in engagement with the generally flat surface such that the double-sided tape 96 is in facing engagement therewith. If it is desired to further secure the mounting bracket 16 to the generally flat surface, fasteners can then be disposed through the apertures 96 into the generally flat surface for further securing the mounting bracket 16 to the generally flat surface.

The container 10 is now ready to be mounted on the mounting bracket 16. However, it is first preferred that the sterilization agent 12 be deposited within the container 10. Preferably, the sterilization agent 12 is deposited within the sterilization agent compartment 60 through the first access opening 36 (i.e., the bore of the filler neck 37) and flows through a portion of the openings 56 in the first partition 52 into the reservoir 54. Upon the reservoir 54 being filled with the sterilization agent 12, the sterilization agent 12 flows through another portion of the openings 56 in the first partition 52 into the toothbrush holder compartment 62 to thereby sterilize any toothbrushes 14 therein.

In the present embodiment, it is preferred that the sterilization agent 12, and the toothbrush holder compartment 62 be of sufficient depth in order to accomplish proper sterilization. That is, it is preferred that the level of sterilization agent 12 be of sufficient depth to cover the bristles 15 of the toothbrushes 14, as shown in FIG. 2. The depth of the sterilization agent 12 can be monitored by lifting the lid member 68 into the open position. After the container 10 is filled to the appropriate level of the sterilization agent 12, the cap 39 is threadably secured to the filler neck 37.

To mount the container 10 on the mounting bracket 16, the L-shaped members 48 are placed proximate the support plate 82 just above the bars 92. The container 10 is then moved downwardly such that the second leg 51 is disposed between the bars 92 and the support plate 82 and the first leg 50 is in engagement with the bars 92. In this position, the container 10 is firmly secured to the mounting bracket 16 and, therefore, the generally flat surface.

To access the toothbrush holder compartment 62, the user merely lifts the lid member 68 by the handle 70 to place the same in the open position. When the toothbrushes 14 are placed in their respective individual toothbrush receiver compartments 64, the lid member 68 should be placed in the closed position for inhibiting the entry of foreign matter into the container 10 and inhibiting evaporation of the sterilization agent 12. The use of the mounting bracket 16 in conjunction with the container 10 allows the sterilization agent 12 to be readily changed, that is, by removing the container 10 from the mounting bracket 16, the container 10 is easily cleanable and can be placed over a sink or the like when depositing the sterilization agent 12 therein to capture any spillage during the filling process.

From the foregoing description, it can be seen that the present invention comprises a durable, low cost toothbrush sterilization container for sterilizing toothbrushes and a mounting bracket for attaching the container to a generally flat surface. It will be appreciated by those skilled in the art that changes could be made to the embodiment described above without departing from the broad inventive concept thereof. It is understood, therefore that this invention is not limited to the particular embodiment disclosed, but is intended to cover all modifications which are within the spirit and scope of the invention as defined by the appended claims.

I claim:

1. A toothbrush sterilization container for receiving a sterilization agent and at least one toothbrush, said container comprising:

a bottom wall having a first edge, a second edge, a third edge, and a fourth edge;

a top wall having a first edge, a second edge, a third edge, and a fourth edge; said top wall being positioned generally parallel to and spaced from said bottom wall; said top wall having a first access opening for adding and removing said sterilization agent from said container;

a first side wall extending between and attached to said first edges of said top and bottom walls such that said first side wall extends generally perpendicularly from said top and bottom walls;

a second side wall extending between and attached to said second edges of said top and bottom walls such that said second side wall extends generally perpendicularly from said top and bottom walls;

a front wall extending from said third edge of said bottom wall such that a second access opening for adding and removing toothbrushes from said container is formed between said front and top walls and said front wall extends generally perpendicularly from said bottom wall;

a rear wall extending between and attached to said fourth edges of said top and bottom walls such that said rear wall extends generally perpendicularly from said top and bottom walls, said rear wall having a bracket means for attaching said container to a mounting bracket;

a first partition positioned between and spaced from said top and bottom walls and in complementary engagement with said front wall, said rear wall, said first side wall and said second side wall such that a reservoir is formed between said bottom wall, said first partition, said first side wall, said front wall, said second side wall, and said rear wall, said first partition including openings therethrough for permitting said sterilization agent to pass to and from said reservoir;

a second partition positioned between and spaced from said front and rear walls and in complementary engagement with said first partition, said top wall, said first side wall and said second side wall such that a sterilization agent compartment is formed between said second partition, said rear wall, said first partition, said top wall, said first side wall, and said second side wall and a toothbrush holder compartment is formed between said second partition, said first partition, said front wall, said first side wall, and said second side wall;

divider means positioned within said toothbrush holder compartment for dividing said toothbrush holder compartment into individual toothbrush receiver compartments and interior portions thereof;

a lid member for being pivotally mounted to said top wall;

a hinge means interconnected between said lid member and said top wall for allowing said lid member to pivot with respect to said top wall between a first position wherein said lid member is positioned proximate said second access opening and a second position wherein said lid member is positioned away from said second access opening; and a shelf member extending from said bottom wall for receiving a toothpaste tube, whereby said sterilization agent deposited within said sterilization agent compartment through said first access opening flows through a portion of said openings in said first partition into said reservoir and upon said reservoir being filled with said sterilization agent, said sterilization agent flows through another portion of said openings in said first partition into said toothbrush receiver compartment to thereby sterilize any toothbrushes therein.

2. The toothbrush sterilization container according to claim 1, wherein said first access opening comprises a filler neck and cap for being releasably positioned thereon.

3. The toothbrush sterilization container according to claim 1, further including a handle positioned on said lid member.

4. A combination toothbrush sterilization container and mounting bracket for attaching said toothbrush sterilization container to a generally flat surface, said combination comprising:

a toothbrush sterilization container for receiving a sterilization agent and at least one toothbrush, comprising:

a bottom wall having a first edge, a second edge, a third edge, and a fourth edge;

a top wall having a first edge, a second edge, a third edge, and a fourth edge; said top wall being positioned generally parallel to and spaced from said bottom wall; said top wall having a first access opening for adding and removing said sterilization agent from said container;

a first side wall extending between and attached to said first edges of said top and bottom walls such that said first side wall extends generally perpendicularly from said top and bottom walls;

a second side wall extending between and attached to said second edges of said top and bottom walls such that said second side wall extends generally perpendicularly from said top and bottom walls;

a front wall extending from said third edge of said bottom wall such that a second access opening for adding and removing toothbrushes from said container is formed between said front and top walls and said front wall extends generally perpendicularly from said bottom wall;

a rear wall extending between and attached to said fourth edges of said top and bottom walls such that said rear wall extends generally perpendicularly from said top and bottom walls, said rear wall having a bracket means for attaching said container to said mounting bracket;

a first partition positioned between and spaced from said top and bottom walls and in complementary engagement with said front wall, said rear wall, said first side wall and said second side wall such that a reservoir is formed between said bottom wall, said first partition, said first side wall, said front wall, said second side wall, and said rear wall, said first partition including openings therethrough for permitting said sterilization agent to pass to and from said reservoir;

a second partition positioned between and spaced from said front and rear walls and in complementary engagement with said first partition, said top wall, said first side wall and said second side wall such that a sterilization agent compartment is formed between said second partition, said rear wall, said first partition, said top wall, said first side wall, and said second side wall and a toothbrush holder compartment is formed between said second partition, said first partition, said front wall, said first side wall, and said second side wall;

divider means positioned within said toothbrush holder compartment for dividing said toothbrush holder compartment into individual toothbrush receiver compartments and interior portions thereof;

a lid member for being pivotally mounted to said top wall;

a hinge means interconnected between said lid member and said top wall for allowing said lid member to pivot with respect to said top wall between a first position wherein said lid member is positioned proximate said second access opening and a second position wherein said lid member is positioned away from said second access opening; and a shelf member extending from said bottom wall for receiving a toothpaste tube, whereby said sterilization agent deposited within said sterilization agent compartment through said first access opening flows through a portion of said openings in said first partition into said reservoir and upon said reservoir being filled with said sterilization agent, said sterilization agent flows through another portion of said openings in said first partition into said toothbrush holder compartment to thereby sterilize any toothbrushes therein; and a mounting bracket for attaching said container to said generally flat surface, comprising:

a support plate having a first side edge and a second side edge;

a first side plate extending from said first side edge of said support plate such that said first side plate and said support plate are generally perpendicular with respect to each other;

a second side plate extending from said second side edge of said support plate such that said first side plate and said support plate are generally perpendicular with respect to each other and said first side plate and said second side plate are generally parallel with respect to each other;

a bar extending between said first side plate and said second side plate, said bar being spaced from said support plate a predetermined distance to thereby define a space therebetween for complementarily receiving said bracket means within said space when said container is positioned on said mounting bracket; and mounting means positioned on said support plate for attaching said support plate to said generally flat surface.

5. The combination according to claim 4, wherein said mounting means is comprised of double-sided tape disposed between said support plate and said generally flat surface.

6. The combination according to claim 4, wherein said mounting means is comprised of a fastener positioned through an aperture in said support plate, said fastener for being secured to said generally flat surface.

7. The combination according to claim 4 wherein said bracket means comprises a generally L-shaped member extending from said rear wall, said L-shaped member including a first leg extending from said rear wall and a second leg for being positioned within said space between said support plate and said bar extending between said first side plate and said second side plate.

* * * * *